United States Patent
Reinshagen et al.

(10) Patent No.: US 9,901,426 B2
(45) Date of Patent: Feb. 27, 2018

(54) PRODUCTION OF DENTAL SHAPED PARTS COMPOSED OF POROUS GLASS

(75) Inventors: Jörg Reinshagen, Pforzheim (DE); Sascha Cramer Von Clausbruch, Mühlacker-Lienzingen (DE); Michael Winterling, Büren (DE)

(73) Assignee: Ivoclar Vivadent AG, Schaan (LI)

( * ) Notice: Subject to any disclaimer, the term of this patent is extended or adjusted under 35 U.S.C. 154(b) by 818 days.

(21) Appl. No.: 13/993,972

(22) PCT Filed: Dec. 19, 2011

(86) PCT No.: PCT/EP2011/073255
§ 371 (c)(1),
(2), (4) Date: Jan. 9, 2014

(87) PCT Pub. No.: WO2012/080513
PCT Pub. Date: Jun. 21, 2012

(65) Prior Publication Data
US 2014/0120297 A1    May 1, 2014

(30) Foreign Application Priority Data

Dec. 17, 2010 (DE) .......................... 10 2010 056 037

(51) Int. Cl.
*A61C 13/00*  (2006.01)
*A61K 6/027*  (2006.01)
(Continued)

(52) U.S. Cl.
CPC .......... *A61C 13/0022* (2013.01); *A61C 13/08* (2013.01); *A61K 6/0276* (2013.01); *A61K 6/033* (2013.01); *C03B 19/06* (2013.01); *C03C 4/0021* (2013.01); *C03C 11/00* (2013.01); *Y10T 428/21* (2015.01)

(58) Field of Classification Search
CPC ... Y10T 428/21; A61C 13/0022; A61C 13/08; A61K 6/0276; A61K 6/033
See application file for complete search history.

(56) References Cited

U.S. PATENT DOCUMENTS 5,653,791 A    8/1997   Panzera et al.
6,280,863 B1   8/2001   Frank et al.
(Continued)

FOREIGN PATENT DOCUMENTS

CA   2239865 A2   6/1998
CA   2380576 C    2/2001
(Continued)

*Primary Examiner* — Gerard Higgins
(74) *Attorney, Agent, or Firm* — Ann M. Knab; Thad McMurray

(57) ABSTRACT

The invention discloses a blank for producing dental shaped parts which consists entirely of porous glass without crystalline portions. The density of the blank is between 50% and 95% of its theoretical density. It has a discoidal shape with a diameter of at least 20 mm. The blank is produced by a process in which glass powder is first pressed at a pressure of between 10 MPa and 300 MPa and this green body is (pre-)sintered at a temperature of between 580° C. and 750° C. to form a blank of porous glass without crystalline portions. From the obtained blank, monolithic dental shaped parts can be obtained by mechanical processing followed by sintering, wherein a process according to the invention for stabilizing the shape of the shaped parts is used.

12 Claims, 2 Drawing Sheets

Figure 1:
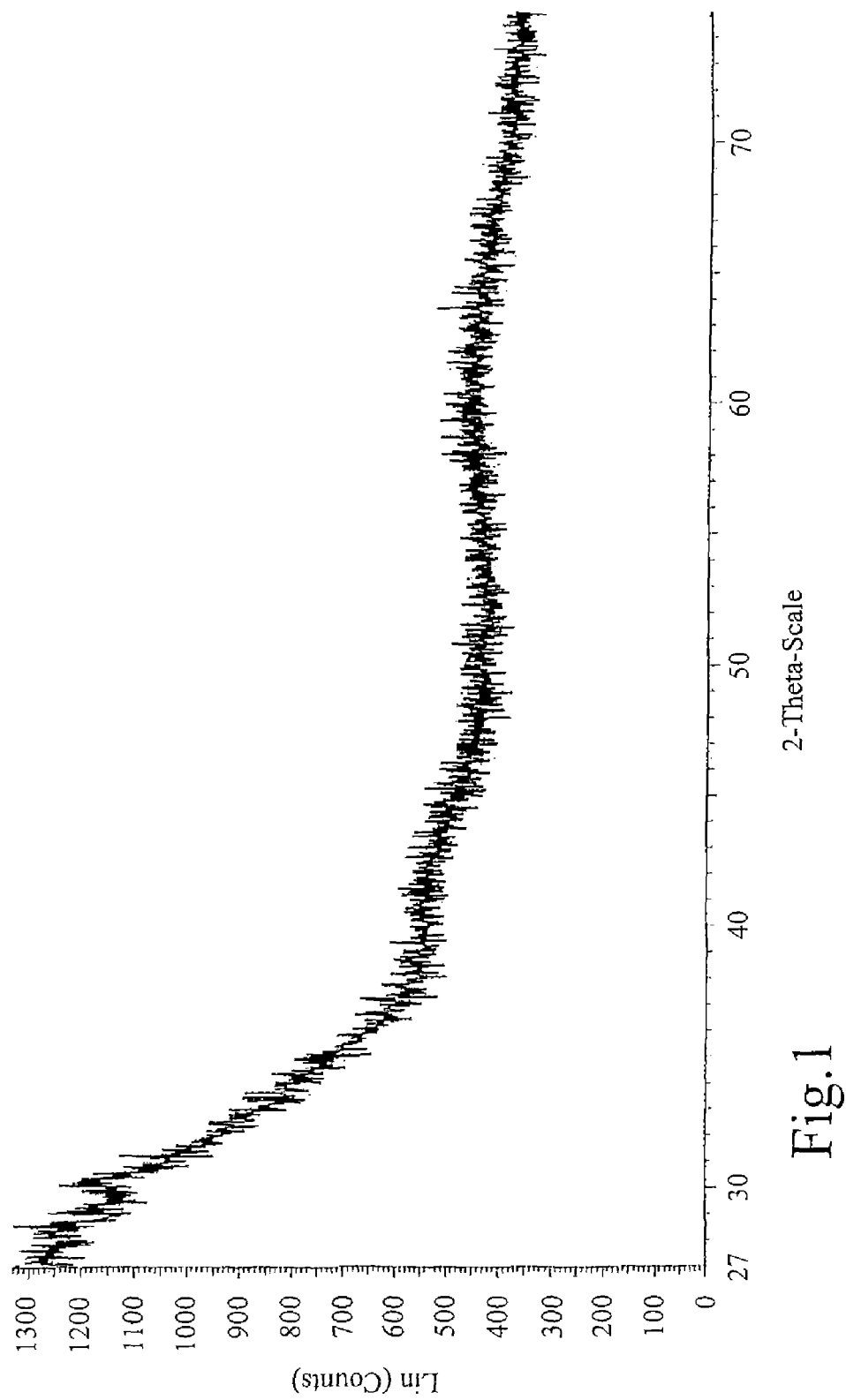

(51) Int. Cl.
  *C03B 19/06* (2006.01)
  *C03C 4/00* (2006.01)
  *C03C 11/00* (2006.01)
  *A61C 13/08* (2006.01)
  *A61K 6/033* (2006.01)

(56) References Cited

U.S. PATENT DOCUMENTS

| | | |
|---|---|---|
| 6,342,302 B1 | 1/2002 | Steidl et al. |
| 6,354,836 B1 | 3/2002 | Panzera et al. |
| 7,604,759 B2 | 10/2009 | Gubler et al. |
| 2010/0035215 A1 | 2/2010 | Brodkin et al. |
| 2010/0248189 A1 | 9/2010 | Burger et al. |
| 2011/0021336 A1 | 1/2011 | Bolle et al. |

FOREIGN PATENT DOCUMENTS

| | | |
|---|---|---|
| DE | 198 52 516 A1 | 5/2000 |
| EP | 0824897 A2 | 2/1998 |
| EP | 0 885 855 A2 | 12/1998 |
| EP | 1 025 829 A1 | 8/2000 |
| EP | 2 287 122 A1 | 2/2001 |
| EP | 2 387 984 A1 | 11/2011 |
| WO | 2004/086999 A1 | 10/2004 |

PRODUCTION OF DENTAL SHAPED PARTS COMPOSED OF POROUS GLASS

CROSS-REFERENCE TO RELATED APPLICATIONS

This application is a National Stage application of International patent application PCT/EP2011/073255, filed on Dec. 19, 2011, which claims priority to German patent application No. 102010056037.5, filed on Dec. 17, 2010, the disclosures of which are incorporated herein by reference in their entirety.

The invention firstly relates to a blank for producing dental shaped parts as well as a process for producing this blank. The invention furthermore relates to a process for stabilizing the shape of a monolithic dental shaped part during the production thereof as well as a process for producing monolithic dental shaped parts and the monolithic dental shaped parts themselves.

In recent years, ceramic or all-ceramic dental prostheses have become increasingly important. With this type of dental prostheses, the ceramic material is not only used for veneering metal frameworks, as previously known, but the framework material itself is also made from ceramic. In this way, all-ceramic dental prostheses, for example all-ceramic crowns and all-ceramic bridges, are achieved. In this connection, zirconium dioxide in particular is to be emphasized as ceramic material.

In the case of all-ceramic dental prostheses, the frameworks, but also other dental shaped parts such as veneers, abutments (implant structural parts) or even whole teeth, as a rule are machined, in particular milled, from a ceramic block (blank). Such blanks can in principle consist of (finally-)sintered ceramic material which no longer changes its dimensions during further heat treatment. However, a disadvantage here is that such a material can be mechanically processed only with difficulty because of its hardness.

The use of blanks made of an unsintered or not (finally-)sintered ceramic material has therefore proved advantageous. Such materials can be machined dry and are disclosed for example in WO-A1-2004/086999. These materials are used in conjunction with a CAD/CAM technique, which already takes into account the sintering shrinkage of the material during the final-sintering for the machining of the dental prostheses from the blank.

A process for producing a veneer for a dental prosthesis as well as the dental prosthesis itself are described in US 2010/0248189 A1. A precursor of the veneer is produced from a blank, and this blank or this precursor consists of a porous glass ceramic or a porous glass. The disclosure of this document relates expressly to veneers, i.e. to dental shaped parts which, together with a further part, as a rule together with a framework, form the finished dental prosthesis.

Different materials for preparing blanks are already known for the mentioned intended uses. However, there is a further need for such materials, in particular ones that can be machined, in particular milled, dry, i.e. without cooling lubricants.

Furthermore, as far as the applicant is aware, the problem of preparing a monolithic glass dental prosthesis from a porous glass blank that can be milled dry has not been solved. This is because, among other things, during the sintering step necessary to reduce its porosity, glass tends to flow. However, as a dental shaped part, it thus loses its adaptation to the shape of the prepared tooth stump, which is why monolithic dental prosthesis parts made of glass have not been used commercially until now.

This object is achieved firstly by the blank with the features of claim 1 as well as by the process with the features of claim 9. Preferred embodiments of the blank are defined in the dependent claims 2 to 8. The wording of all claims, including those discussed below, is hereby incorporated into the content of this description by reference.

The blank according to the invention for producing dental shaped parts is characterized in that it consists entirely of porous glass without crystalline portions. The density of this porous blank is between 50% and 95% of its theoretical density (in the densely-sintered state). The blank further has a disc-like shape with a diameter of at least 20 mm.

By "blank" is meant any body of the named geometry from which dental shaped parts can be machined, preferably by a mechanical processing such as milling, cutting, and similar. Such blanks are often also called "ingots".

By "disc-like shape" is meant according to the invention any geometric design of the blank according to the invention in which the corresponding body has a much smaller or substantially smaller thickness than the defined diameter of at least 20 mm. The term "disc-like" is intended to express that the invention is not limited to round, i.e. substantially circular, disks, but is also intended to include deviations from the circular shape. These can include for example blanks with oval cross-sectional surfaces, for example elliptical cross-sectional surfaces. Other cross-sectional surfaces with at least partially curved circumferential lines are also intended to be comprised, such as for example disks the outer circumference of which emulates the outer contour of a horseshoe.

By "glass" is meant an amorphous, non-crystalline solid. It is an amorphous substance which can be described thermodynamically as frozen, supercooled liquid.

The glasses according to the invention are preferably oxidic glasses, and in particular borosilicate glasses or aluminosilicate glasses. Alkali borosilicate glasses are particularly suitable for the present invention, as they can be prepared particularly well as amorphous, porous solid bodies. By definition, such alkali borosilicate glasses include, as constituents, alkali metal oxides, as a rule sodium oxide ($Na_2O$) and/or potassium oxide ($K_2O$) and boron trioxide ($B_2O_3$). Further constituents, as a rule main constituents, are silicon dioxide ($SiO_2$) and aluminium oxide ($Al_2O_3$).

By "porous" is meant in accordance with the invention that the glass, of which the blank consists, has pores, preferably microscopically small pores. As a rule, the individual pores are at least partially connected to one another, with the result that an open-pored system is present. The pore size in porous glasses can be varied within wide limits, in particular through the production process, with the result that pore sizes between 0.5 nm and 5000 nm are possible. The pore-size distribution can also be set more or less broad.

By "density" is meant in accordance with the invention, in the usual way, the weight of the glass (in gram g) per $cm^3$. The theoretical density is the value of the density at which the glass is substantially pore-free. In relation to the blank, this is the state in which the blank is densely-sintered and thus largely pore-free.

In a further embodiment, the density of the blank according to the invention is preferably between 55% and 85%, in particular between 70% and 80%, of the theoretical density of the blank.

As already explained, in particular silicate glasses such as borosilicate glasses, preferably alkali borosilicate glasses, can be used in the invention. Such glasses can advantageously be consisting of the following components:

| | |
|---|---|
| $SiO_2$ | 50-80 wt.-% |
| $Al_2O_3$ | 3-24 wt.-% |
| $K_2O$ | 3-13 wt.-% |
| $Na_2O$ | 3-13 wt.-% |
| $Li_2O$ | 0-4 wt.-% |
| $B_2O_3$ | 0-4 wt.-% |
| F | 0-4 wt.-% |
| $TiO_2$ | 0-8 wt.-% |
| $ZrO_2$ | 0-8 wt.-% |
| $P_2O_5$ | 0-4 wt.-% |
| $SnO_2$ | 0-4 wt.-% |
| MgO | 0-4 wt.-% |
| CaO | 0-4 wt.-% |
| BaO | 0-4 wt.-% |
| $Sb_2O_3$ | 0-4 wt.-% |
| $CeO_2$ | 0-8 wt.-%. |

In the invention, blanks in which the porous glass used is consisting of either the components

| | |
|---|---|
| $SiO_2$ | 55-65 wt.-% |
| $Al_2O_3$ | 17-24 wt.-% |
| $K_2O$ | 5-9 wt.-% |
| $Na_2O$ | 7-11 wt.-% |
| $Li_2O$ | 0-1 wt.-% |
| $B_2O_3$ | 0-2 wt.-% |
| F | 0-1 wt.-% |
| $TiO_2$ | 0-1 wt.-% |
| $ZrO_2$ | 0-2 wt.-% |
| $P_2O_5$ | 0-1 wt.-% |
| $SnO_2$ | 0-1 wt.-% | or the components

| | |
|---|---|
| $SiO_2$ | 55-80 wt.-% |
| $Al_2O_3$ | 7-23 wt.-% |
| $K_2O$ | 3-10 wt.-% |
| $Na_2O$ | 3-13 wt.-% |
| $Li_2O$ | 0-1 wt.-% |
| $B_2O_3$ | 0-4 wt.-% |
| F | 0-1 wt.-% |
| $TiO_2$ | 0-1 wt.-% |
| $ZrO_2$ | 0-8 wt.-% |
| $P_2O_5$ | 0-1 wt.-% | are further preferred.

In particular, the blank according to the invention has the shape of a substantially circular disk with a diameter of at least 20 mm. Diameters of at least 50 mm are still further preferred. Diameters of at least 80 mm are also advantageously possible.

In the case of all disc-like blanks, in particular in the case of the last-mentioned disks which are substantially circular, the thickness of the disk is in particular greater than 5 mm. Thicknesses of the disks of between 5 mm and 30 mm are still further preferred.

The blanks according to the invention can have the colour that is predefined by the porous glass used to produce them. However, the blanks can advantageously also be coloured. This can be carried out by adding additives to the glass which influence the colouration of the glass.

Thus, colouring additives, in particular metal oxides and other metal salts, can already be added to the glass during its production or to the blank during its production. The corresponding metals can be for example the rare earth elements or the subgroup elements of the periodic table of elements. These metals are preferably iron, chromium, aluminium, tin, zinc, vanadium, selenium, silver, indium, neodymium, samarium, europium, praseodymium, cobalt, nickel, manganese, erbium or cerium.

It is also possible to colour the blanks after their production, for example using dye solutions which contain the mentioned elements in the form of ions or complex ions.

Furthermore, the so-called ceramic pigments can also be used as colouring additives to colour the glass. Such pigments are likewise known to a person skilled in the art. They are oxides and silicates with crystalline structure, for example of the type spinel, zirconium among others. There are, on the one hand, the pigments in which the crystals have an intrinsic colour and, on the other hand, the so-called inclusion pigments in which colourless crystals have coloured inclusions.

In the case of the mentioned coloured blanks according to the invention, the whole blank can be uniformly coloured. However, it is also possible to colour individual parts of the blank or the whole blank differently and to produce for example a continuous colour gradient inside the blank.

In a further embodiment, the blank according to the invention can have at least one holding means for clamping the blank during its processing to form a dental shaped part. This holding means thus serves to (as a rule reversibly) hold or secure the blank in a corresponding processing machine, for example a milling machine.

The at least one holding means is preferably formed directly on the blank, for example also via a fixing such as a bonding, or shaped, such as for example via at least one recess, in particular groove, running at least partially on the outer circumference of the blank.

In addition to the described blank itself, the invention also relates to a process for producing such a blank. This process is characterized in that glass powder is pressed at a pressure of between 10 MPa and 300 MPa to form a green body and this green body is then sintered (pre-sintered) at a temperature of between 580° C. and 750° C. to form a blank made of porous glass (without crystalline contents).

The mentioned pressure applied during the pressing is preferably between 50 MPa and 250 MPa, in particular between 100 MPa and 200 MPa.

The temperature during pre-sintering is preferably between 580° C. and 700° C., in particular between 620° C. and 660° C.

The duration of the temperature treatment during pre-sintering, i.e. the so-called holding times, is between 0.5 h and 10 h, in particular between 1 h and 5 h. Within the last-mentioned range, holding times of between 1 h and 3 h are further preferred.

Finally, it is to be emphasized that the pre-sintering can take place under reduced atmospheric pressure or under vacuum.

With regard to the pressing process, all methods that can be used to press such glass powders can be used. The glass powder is preferably pressed dry. A uniaxial pressing, i.e. application of the pressing pressure in axial direction from one side, or a biaxial pressing, i.e. application of the pressing pressure in axial direction from both one side and the other, is possible.

An isostatic pressing, i.e. application of the pressing pressure from all directions, or a quasi-isostatic pressing, i.e. a combination of axial pressing and pressing on the outer circumference, is also possible.

The invention further relates to a process for stabilizing the shape of a monolithic dental shaped part during its production, wherein this production comprises at least one sintering step.

By "monolithic" is meant any dental shaped part consisting of only one part, which forms a complete dental prosthesis for the corresponding application. Accordingly, monolithic also means unitary or in one piece. This definition expresses the difference compared with a two- or multi-part dental prosthesis which consists for example of a framework and a veneer fitted onto this framework.

Accordingly, the monolithic dental shaped parts according to the invention or the monolithic dental prosthesis can be crowns, bridges, inlays, onlays or the like (consisting of one piece). All these parts can be inserted by the dentist directly into the mouth of the patient.

According to the invention, the shape-stabilization process is characterized in that the monolithic shaped part is connected to at least one support structure or to at least one support mould during at least one time segment within the duration of the sintering, namely such that the change in shape of the shaped part occurring during this sintering is (spatially) limited by the support structure or the support mould.

In other words: The support structure or the support mould prevents the change in shape of the dental part occurring during the sintering process (sintering shrinkage) from exceeding the dimension predetermined by the support structure/support mould.

The described shape-stabilization process is preferably designed such that the shaped part is connected to the support structure/support mould at least during a time segment at the end of the entire duration of the sintering. It is thereby achieved that the limitation of the change in shape of the dental part by the support structure/support mould is guaranteed at least at the end of the sintering process. In such cases, sintering can thus be carried out without support structure/support mould over a first, optionally longer, period and thus a (non-influenced) change in shape of the dental part can be accepted, followed by sintering with support structure/support mould during a second, optionally shorter, time segment at the end of the sintering process. The change in shape, i.e. the sintering shrinkage, as explained above, is then limited in the desired manner at the end of the sintering process.

In this connection, it is also possible to work with several support structures/support moulds of different geometries or different dimensions during a complete sintering process. In these cases, the change in shape of the dental part can then be limited by a first support structure/support mould during a first time segment and then by a second support structure/support mould with different dimensions (etc.) in a next time segment. In this way, the dental part is approximated stepwise to its final shape (after sintering) during the sintering process.

This stepwise procedure can also take its course such that individual parts or sections of the shaped part are brought successively into the desired final shape by support structures/support moulds of different geometries, limiting the change in shape for this part/section.

Depending on the procedure during the described shape-stabilization process, it can be preferred that the support structure or the support mould consists of a temperature-resistant material the shape of which itself does not change or only changes a little during the sintering. The change in shape of the temperature-resistant material in such cases is preferably less than 2 vol.-%, in particular less than 1 vol.-%.

In a further embodiment, the shape-stabilization process can also be designed such that the support structure or the support mould consists of a material the change in shape of which during the sintering, i.e. its sintering shrinkage, corresponds to the change in shape of the dental shaped part during sintering, i.e. its sintering shrinkage. Support structure/support mould on the one hand and dental shaped part on the other thereby change their shape in the same way during the sintering, with the result that for example a form fit between support structure/support mould and dental shaped part at the start of the sintering is preserved during the sintering process until the end of the sintering. Optionally, in such cases, the change in shape of the dental shaped part during sintering can also be controlled by the change in shape of the support structure/support mould during the sintering, for example by intentionally selecting for the material of the support structure/support mould a shrinkage behaviour other than the shrinkage behaviour displayed by the dental shaped part.

The mentioned temperature-resistant materials for the production of the support structure or the support mould are known in dental engineering as so-called refractory materials. As a rule, they are used as so-called investing compounds. These consist, as a rule, of three essential components, namely a refractory matrix, a preferably inorganic binder and additives. The matrices are typically materials based on $SiO_2$ (quartz and/or cristobalite). Binders are for example aqueous dispersions of ethyl silicate or sodium silicate (waterglass).

As a rule, phosphate-bonded, calcium sulphate-bonded and quartz-bonded investing compounds are used. These compounds are also called investing plasters. Depending on the proportion of the individual components or the composition of the investing compound, an individually adjustable expansion/contraction of the compound during sintering and the maximum temperature resistance of the compound result. Embedding compounds/refractory materials with low expansion (<3%) or with zero-expansion and compounds with a temperature resistance of more than 900° C. or more than 1000° C. are preferred.

Suitable support structures/support moulds can be produced from such materials for example by machining such as milling or by means of casting processes.

Depending on which monolithic shaped part is to be stabilized during the sintering step, the support structure/support mould can be designed differently. If for example it is a monolithic crown, the support structure/support mould is present as a positive mould, preferably in the shape of a tooth stump onto which the crown is fitted at least during some of the sintering process. The shape stabilization between the outer surface of the support structure/support mould, here in the shape of a tooth stump, and the inner surface of the crown is thereby accomplished. The support structure/support mould in the shape of the tooth stump can be obtained for example by duplicating the model which was obtained using the dental imprint or also by milling using digitalized data of the model.

If the monolithic shaped part is for example a so-called inlay, the shape stabilization takes place in that the support structure/support mould forms a negative mould for the dental shaped part. Accordingly, the inner surface of the support structure/support mould here stabilizes the outer surface of the dental shaped part, at least during some of the sintering process.

Finally, the invention relates to a process for producing monolithic dental shaped parts. This process is characterized in that a blank, as described above, is machined (forming a monolithic shaped part as defined above) and the thus-obtained shaped part is sintered (finally-sintered) to at least 98% of its theoretical density using the described shape-stabilization process. The machining preferably takes place by at least one milling step. Furthermore, the machining is in particular a dry machining, i.e. a processing without the use of coolants, such as cooling liquids.

The temperature treatment during the final-sintering preferably takes place over a period (holding times) of between 0.5 min (30 s) and 1 h, in particular between 0.5 min and 20 min. Within the last-mentioned periods, holding times of between 0.5 min and 10 min, in particular between 1 min and 5 min, are further preferred.

The sintering shrinkage of the produced dental shaped part during the final-sintering is, as a rule, below 20% (volume reduction), preferably between 5% and 15%.

The temperature treatment during the final-sintering can advantageously also take place under reduced atmospheric pressure, preferably under vacuum.

The process according to the invention for producing the dental shaped parts is advantageously designed such that the monolithic shaped part after the final-sintering still consists of glass which has essentially no crystalline portions. This is achieved with the correspondingly composed glasses in particular by the type of the temperature treatment (level of the sintering temperature, holding time). Accordingly, only the porosity of the glass, i.e. the number of pores in the glass, is reduced by the final-sintering, without crystalline portions forming in the glass as a result of the temperature treatment.

However, it is also possible, in particular by the process step of the final-sintering and/or by the selection of the constituents of the glass used, to produce crystalline portions in the glass during the final-sintering. In these cases, the monolithic dental shaped part (unlike the blank used for its production) then no longer consists or no longer consists exclusively of amorphous glass after its preparation. It is thus a glass ceramic which, as a rule, has crystalline (ceramic) areas in an amorphous (glass) matrix.

The sintering temperatures during the final-sintering which are maintained during the holding times mentioned as preferred lie in particular between 800° C. and 1100° C. during the production process according to the invention for the dental shaped parts. Sintering temperatures of between 900° C. and 1050° C. are further preferred.

It is also possible in the production process for the dental shaped parts to colour these shaped parts. This is then preferably carried out after the machining before the final-sintering, in particular by means of the above-named dye solutions.

In addition to the mentioned production process for the monolithic dental shaped parts, the invention also relates to the monolithic dental shaped parts themselves, as are or can be obtained by the described process.

These shaped parts are preferably crowns, partial crowns or bridges as well as inlays, onlays or whole teeth.

The so-called CTE value (coefficient of thermal expansion) (measured according to ISO-6872) is in the case of the dental shaped parts according to the invention preferably less than $10 \times 10^{-6}$ 1/K and in particular lies between 7 and $10 \times 10^{-6}$ 1/K.

Further features of the invention result from the following examples in conjunction with the dependent claims. In an embodiment of the invention the individual features can each be realized alone or several features can be combined with each other.

Figure 2:
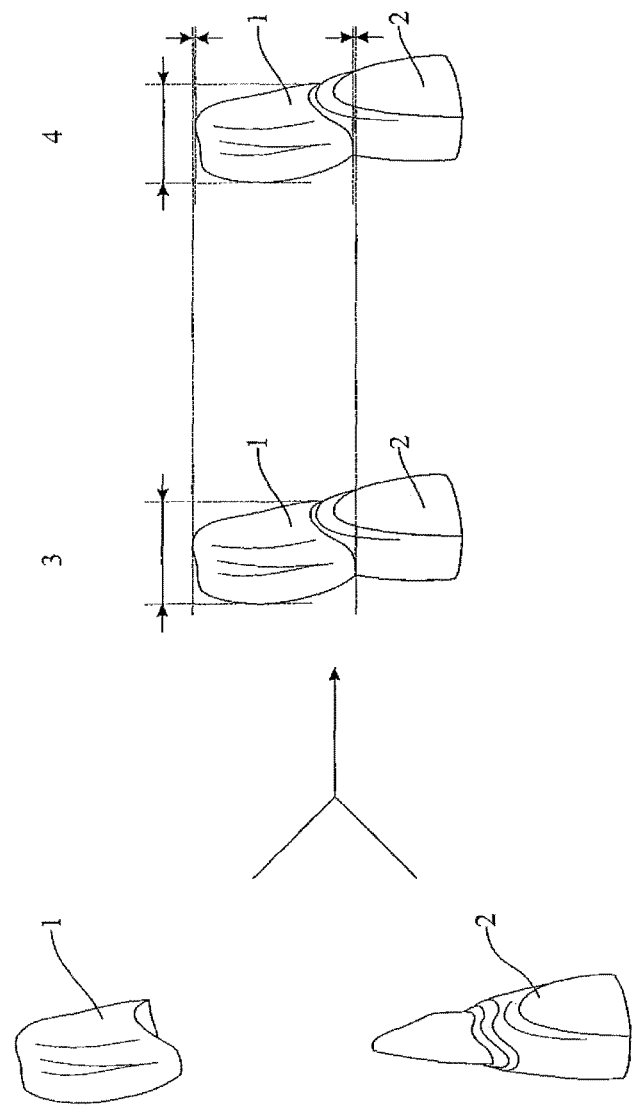

There are shown in the drawings:

FIG. 1 the representation of an X-ray diffractogram of blanks according to the invention, FIG. 2 the schematic representation of an embodiment of the process according to the invention for stabilizing the shape of monolithic dental shaped parts.

EXAMPLE 1

A first glass powder with the chemical composition corresponding to Table 2 and the particle-size distribution corresponding to Table 3 was uniaxially pressed by means of a hydraulic pressing machine to form circular discoidal blanks (green bodies) with a diameter of about 100 mm and a thickness of 18 mm. The pressing force was between 800 kN and 2000 kN, preferably about 1200 kN.

During the production of such discoidal blanks, it is advantageous if the glass powder used for the production is granulated with a binder. As a rule, this is achieved by a so-called spray granulation. Here, the glass powder is processed to form a granular material accompanied by simultaneous mixing with the binder. Such processes are known to a person skilled in the art.

Three groups of blanks were then sintered at atmospheric pressure at 640° C., at 660° C. and at 680° C., respectively, during a holding time of 2 hours (Table 1). The preferred sintering temperature was 640° C. Higher temperatures led to increasingly hard blanks which could only be milled with difficulty (high tool wear). Below 640° C. the blanks became increasingly soft, with the result that the blanks had to be processed and treated carefully. The density of the blanks was 1.79 g/cm$^3$ after the sintering at 640° C., 1.82 g/cm$^3$ after the sintering at 660° C. and 1.87 g/cm$^3$ after the sintering at 680° C.

As explained in the description, the thus-produced blank consists of porous glass without crystalline portions. This is shown in FIG. 1 for the blanks which were produced according to Example 1. FIG. 1 is an X-ray diffractogram which was obtained using the blanks pressed and sintered according to Example 1. The intensity is plotted against the angle in the usual way. FIG. 1 shows no diffraction intensity maxima which would be characteristic for crystalline solids or crystalline portions in such solids. Only the known diffuse dispersion which is characteristic for amorphous substances is shown.

Accordingly, the blanks produced according to Example 1 are amorphous solids without crystalline content.

The blanks sintered at 640° C. were clamped in a holding element and processed by means of CAD/CAM milling processing taking into account the sintering shrinkage. Enlarged crowns corrected for the sintering shrinkage were thus milled from the blanks as monolithic shaped parts. The results are shown in Table 1.

As represented schematically in FIG. 2, the thus-milled crowns 1 (enlarged by the sintering shrinkage) were fitted onto a model die 2 made of non-shrinking refractory material (investing compound Wilavest Quick from the applicant) and sintered onto the die in form-fitting manner in a dental furnace. FIG. 2 shows arrangement 3 of die 2 with fitted crown 1 before the sintering and arrangement 4 of die 2 with fitted crown 1 after the sintering. The sintering shrinkage occurring during sintering, which is about 10% in the present case, is indicated (on the right) by the arrows in arrangement 4.

For easy removal of the crown, the die of refractory material was thinly coated with a high-temperature release agent (BN powder, applied with a brush; alternatively also as a spray). Such a release agent is, however, not strictly necessary. The model die itself was produced by pouring the refractory compound into so-called duplicating moulds or by milling from the corresponding material. After the sintering, transparent and tooth-coloured sintered crowns were obtained which had adapted to the die contour and could easily be released from the die material.

The CTE values of the shaped parts are 9.3±0.5×10⁻⁶ 1/K (25° C. to 500° C.).

TABLE 1

Produced glass blanks from the first glass powder

| No. | Press geometry [mm] | Pressing pressure [kN] | Sintering temperature [° C.] | Density [g/cm³] |
|---|---|---|---|---|
| 1 | 100 mm × 18 mm | 1200 | 640 | 1.79 |
| 2 | 100 mm × 18 mm | 1200 | 660 | 1.82 |
| 3 | 100 mm × 18 mm | 1200 | 680 | 1.87 |

TABLE 2

Chemical composition of the first glass powder

| Substance | Amount [wt.-%] |
|---|---|
| $SiO_2$ | 60.5 |
| $Al_2O_3$ | 22.0 |
| $K_2O$ | 8.0 |
| $Na_2O$ | 9.0 |
| $B_2O_3$ | 0.5 |

The theoretical density of this glass powder is about 2.45 g/cm³.

TABLE 3

Particle-size distribution of the first glass powder

| Distribution | Diameter [μm] |
|---|---|
| d 10 | 1.5 |
| d 50 | 9 |
| d 90 | 45 | d 10, d 50, and d 90 means that 10%, 50% and 90%, respectively, of the particles present are smaller than the indicated value for the diameter.

The invention claimed is:

1. A blank for producing dental shaped parts, characterized in that it consists entirely of porous glass without crystalline portions, wherein the density of the porous glass blank is between 50% and 95% of the theoretical density of the blank when it is in its densely-sintered state, and in that it has a disc-like shape with a diameter of at least 20 mm, wherein the glass consists of the following components:

| $SiO_2$ | 55-65 wt.-% |
|---|---|
| $Al_2O_3$ | 17-24 wt.-% |
| $K_2O$ | 5-9 wt.-% |
| $Na_2O$ | 7-11 wt.-% |
| $Li_2O$ | 0-1 wt.-% |
| $B_2O_3$ | 0-2 wt.-% |
| F | 0-1 wt.-% |
| $TiO_2$ | 0-1 wt.-% |
| $ZrO_2$ | 0-2 wt.-% |
| $P_2O_5$ | 0-1 wt.-% |
| $SnO_2$ | 0-1 wt.-% |
| MgO | 0-4 wt.-% |
| CaO | 0-4 wt.-% |
| BaO | 0-4 wt.-% |
| $Sb_2O_3$ | 0-4 wt.-% |
| $CeO_2$ | 0-8 wt.-%. |

2. The blank according to claim 1, characterized in that the density of the blank is between 55% and 85% of the theoretical density of the blank when it is in its densely-sintered state.

3. The blank according to claim 1, characterized in that the diameter of the disc-like shape is at least 50 mm.

4. The blank according to claim 1, characterized in that the thickness of the disk-like shape is more than 5 mm.

5. The blank according to claim 1, characterized in that the blank has at least one recess for clamping the blank during the processing thereof to form a dental shaped part, wherein the at least one recess is provided on the outer circumference of the blank.

6. The blank according to claim 1, characterized in that the density of the blank is between 70% and 80% of the theoretical density of the blank when it is in its densely-sintered state.

7. The blank according to claim 1, characterized in that the diameter of the disc-like shape is at least 80 mm.

8. The blank according to claim 1, characterized in that the thickness of the disk-like shape is between 5 mm and 30 mm.

9. The blank according to claim 1, characterized in that the ratio of the diameter to the thickness is 4:1.

10. The blank according to claim 1, characterized in that the ratio of the diameter to the thickness is 20:1.

11. Process for producing the blank according to claim 1, characterized in that glass powder is pressed at a pressure of between 10 and 300 MPa to form a green body and said green body is pre sintered at a temperature of between 580° C. and 750° C. to form the blank that consists entirely of the porous glass without crystalline portions.

12. Process for producing the blank according to claim 1, characterized in that glass powder is pressed at a pressure of between 100 and 200 MPa to form a green body and said green body is (pre)sintered at a temperature of between 620° C. and 660° C. to form the blank that consists entirely of the porous glass without crystalline portions.

* * * * *